United States Patent [19]

Fiaschetti

[11] Patent Number: 4,885,157

[45] Date of Patent: Dec. 5, 1989

[54] DERMAL COSMETIC COMPOSITION AND APPLICATIONS THEREFOR

[76] Inventor: Mary G. Fiaschetti, 12206 Cedar Gap La., Houston, Tex. 77072

[21] Appl. No.: 14,302

[22] Filed: Feb. 13, 1987

[51] Int. Cl.$^4$ .......................... A61K 7/40; A61K 7/42; A61K 7/44; A61K 7/48
[52] U.S. Cl. ........................................ 424/59; 424/60; 424/62; 424/195.1; 514/773; 514/776; 514/783; 514/844; 514/847; 514/859; 514/860; 514/861; 514/863; 514/873; 514/886; 514/887; 514/904
[58] Field of Search ............... 514/783, 776, 844, 847, 514/886, 859, 860, 861, 863, 904; 424/59, 60

[56] References Cited

U.S. PATENT DOCUMENTS

| | | | |
|---|---|---|---|
| 3,483,008 | 12/1969 | Herr | 514/776 |
| 4,699,930 | 10/1987 | Suga | 514/887 |
| 4,707,293 | 11/1987 | Ferro | 514/904 |
| 4,737,360 | 4/1986 | Allen et al. | 514/847 |

FOREIGN PATENT DOCUMENTS

| | | | |
|---|---|---|---|
| 2617919 | 11/1976 | Fed. Rep. of Germany | 514/776 |
| 0051109 | 3/1985 | Japan | 514/783 |
| 0181013 | 9/1985 | Japan | 514/776 |
| 843835 | 10/1984 | PCT Int'l Appl. | 514/783 |
| 0971331 | 11/1982 | U.S.S.R. | 514/783 |

OTHER PUBLICATIONS

Hironaka et al 1978, vol. 89, pp. 30599g, Chemical Abstracts.
Hironaka et al. (II), 1978, vol. 89, pp. 30600a, Chemical Abstracts.
Nagodawithana et al, 1985, vol. 103, pp. 140301u, Chemical Abstracts.

*Primary Examiner*—Dale R. Ore
*Attorney, Agent, or Firm*—James L. Jackson & Asoc.

[57] ABSTRACT

Provided is a cosmetic compositiom which beautifies and moisturizes the skin of a human being. The composition may also have therapeutic effects on the human skin such as the removal of lines or wrinkles, dissolution of fat pockets, the removal of bags under the eyes, and the closing of pores or gaps in the skin to render a smooth uniform appearance. The composition is comprised of seven basic ingredients, which include:
  live yeat cells,
  selenium,
  carotene,
  RNA,
  DNA,
  water and
  albumen.

These core ingredients generally make up from about 80% to 100% of the composition used in the treatment, and are the basis for the advantages realized thereby. Significant and long-lasting results are particularly achieved upon application of the composition to the human skin with exposure to sunlight.

16 Claims, No Drawings

DERMAL COSMETIC COMPOSITION AND APPLICATIONS THEREFOR

BACKGROUND OF THE INVENTION

1. Field of the Invention

This invention relates to a dermal cosmetic composition useful in the beautification and moisturization of human skin. The present invention also relates to a method of applying the composition in order to effect such cosmetic results. The present invention also relates to a composition useful in achieving therapeutic effects with regard to skin disorders. The present invention also relates to a method of applying and using such a therapeutic composition.

2. Description of the Prior Art

Many different compositions are available for the beautification of skin and/or the therapeutic treatment of skin disorders. The components of these compositions are many and vary greatly from composition of composition. Different combinations of components are continuously tried in order to achieve specific desired results.

The use of metals, for example, is well known to effect beneficial therapeutic results. See, e.g., U.S. Pat. No. 4,340,590, wherein the use of selenium containing compounds exhibit therapeutic benefits in mammel hosts. The use of selinium and vitamin E has also been reported to have a beneficial effect in the relief of arthritis and tendonitis. The combination of selenium and carotene has also been found to be beneficial in negating the effects of carcinogens. See, e.g., U.S. Pat. No. 4,599,234.

In general, however, the various combinations of components used in beautifying compositions have heretofore not been totally satisfactory in providing the proverbial fountain of youth. The search for a dermal cosmetic composition which can beautify and moisturize the skin and lend to it a youthful glow, as well as possibly achieving the elimination of pock marks, gaps, wrinkles, etc., is continuously ongoing. Different alternatives are constantly flooding the market. The existence of a dermal composition which could also reduce undesirable scar tissue, extended birthmarks, recessions in the skin, as well as treat skin disorders such as psoriasis and eczema, would also be of great benefit to the public welfare. The reduction and alleviation of such skin defects would certainly be a desirable result.

Accordingly, there is provided by the present invention a dermal cosmetic composition which is novel and which cosmetically beautifies and moisturizes the skin.

Another object of the present invention is to provide a method for applying such a novel cosmetic composition in a manner so as to elicity its cosmetic benefits.

Another object of the present invention is to provide a composition which can treat undesirable skin disorders effectively and efficiently.

Still another object of the present invention is to provide a method for the application of such a composition in order to effect such therapeutic results.

These and other objects, as well as the scope, nature and utilization of the invention, will be apparent to those skilled in the art from the following description and the appended claims.

SUMMARY OF THE INVENTION

In accordance with the foregoing objectives, provided herewith is a composition comprised of seven ingredients, i.e., live yeast cells, selenium, carotene, RNA, DNA, water and albumen. This basic composition can be used alone or in combination with other components such as amino acids, vitamins and minerals. The particular combination of supplemental ingredients with the basic composition can be varied depending on the particular effect desired to be elicited, e.g., whether purely cosmetic or therapeutic in nature.

The method of treatment involving the composition comprises merely smoothing the formulated composition over that area to be treated, preferably in a multilayer, e.g., three layer application, and allowing the composition to remain in place. The composition is then removed after the desired length of time.

In a most preferred embodiment, the composition is exposed to sunlight, whether artificial or natural, for a period of time after application. This period of time is generally in the range of from 15 to about 60 minutes. While the exposure to the sunlight is not necessary in order to enjoy the benefits of he present invention, the exposure does surprisingly increase the benefits of the composition with regard to the extent, significance, and lasting effect of the results of the treatment.

DETAILED DESCRIPTION OF THE PREFERRED EMBODIMENTS

The seven components of the basic composition of the present invention for use in the treatment of skin comprises live yeast cells (preferably saccharomyces cerevisial), selenium (preferably powdered), carotene (beta), RNA, DNA, water and albumen. While any combination of the foregoing components in amounts sufficient to provide a composition beneficial for dermal application is contemplated within the present invention, it has been found that beneficial results are obtained when the seven components are combined in the following preferred, and particularly most preferred, amounts:

|  | Preferred | Most Preferred |
| --- | --- | --- |
| Live yeast cells (saccharomyces cerevisial) | 5–8 parts | about 6 parts |
| Selenium (powdered) | $\frac{1}{4}$–$\frac{3}{4}$ parts | about $\frac{1}{2}$ part |
| Carotene (beta) | $\frac{3}{4}$–$1\frac{1}{2}$ part | about 1 part |
| RNA | 2–4 parts | about 3 parts |
| DNA | 1–3 parts | about 2 parts |
| Water | 2–6 parts | about 3 parts |
| Albumen | $\frac{3}{4}$–$2\frac{1}{2}$ parts | about 1 part |

This basic composition is particularly beneficial in eliciting cosmetic effects in the skin, particularly when applied to the face of a human. The composition moisturizes and beautifies the skin, thus resulting in an even coloration and flow of the skin. The amounts of the components used in any particular composition, of course, can be altered to suit the particular skin to which it is applied, with the skin of all humans being somewhat different. Generally, however, it has been found that when the components are used within the amounts described above, beneficial cosmetic effects are achieved upon dermal application.

Depending on the particular amount of components used in the basic composition, therapeutic effects can also be elicted upon dermal application of the composition. Such therapeutic dermal effects can include the removal of lines or wrinkles, the dissolution of fat pockets, the removal of bags under the eyes, the closing of pores or gaps in the skin to render a smooth uniform appearance, the treatment of psoriasis and eczema, as well as a substantial reduction or alleviation of scars and birthmarks. Again, the particular amounts of components employed in any composition suitable for a particular person will differ from person to person.

The method for employing the composition in the treatment of skin is simply the application of the composition to the area which requires treatment. Upon allowing the composition to remain on that area for the desired length of time, i.e., that time sufficient to elicit the cosmetic and/or therapeutic effects desired, the composition is then removed. In a most preferred embodiment, the composition can be applied in layers, whether two or three or more layers. For example, the first layer can be applied as a very thin layer with the composition actually being massaged into the skin during application. A second layer can then be applied as a thin covering layer over the area to be treated, with a third and final layer then being used to totally cover the skin. In general, the length of time of any one treatment runs from 15 to about 60 minutes in length, however longer periods or shorter periods of time can be used if appropriate, and of course will depend on the particular case involved. The length of time in general will vary from person to person being treated. It is most preferred, however, that the length of treatment be in the range of from about 20 to 40 minutes. Removal of the composition is accomplished simply by wiping off the composition with a suitable cloth or other aid which facilitates the removal. This treatment is repeated periodically as desired or necessary.

In a most preferred embodiment, the composition, after application to the skin, is exposed to sunlight. This exposure can be for a specific length of time within the total treatment time, but can also be for the duration of the treatment time. The exposure to sunlight, therefore, generally comprises a length of time ranging from 15 to about 60 minutes, with an exposure of from about 20 to 25 minutes being most preferred. The sunlight employed can be natural sunlight or any suitable artificial sunlight. This exposure to light apparently activates the composition in such a manner, in a sense working or acting as a catalyst, to provide beneficial results in a shorter period of time, and with the results being more significant and longer lasting than if sunlight exposure was omitted. Upon exposure to sunlight, the quality, impact, degree of change and consistency of effect for any individual is greatly increased over a treatment without exposure to sunlight.

In addition to the base composition, various additional ingredients can be added to the composition. Among these ingredients are various amino acids, vitamins and minerals. These additional ingredients can be added in order to supplement the beneficial effects which are obtained from the base composition. The amounts of these additional ingredients can vary greatly, and will depend upon the specific result one wishes to elicit and the type of skin to which the composition will be applied.

In general, when additional ingredients are added to the base composition, the base composition does comprise at least 80% of the overall composition, with the additional ingredients comprising the remaining 20%. It is more preferred that the base composition comprise at least 85%, and more preferably 90% of the overall composition, with the additional supplemental ingredients comprising the remaining 15%, and most preferably 10%. All of the ingredients can be mixed together by conventional mixing means, and all of the ingredients including those of the base composition are commercially available on the open market.

Of the additional ingredients which can be added and have been found to be beneficial as supplemental ingredients to the base composition, the following are examples:

| | |
|---|---|
| Alanine | Folic acid |
| Arginie | Vitamin $B_1$ |
| Aspartic acid | Vitamin $B_2$ |
| Serine | Niacin |
| Threonine | Vitamin $B_6$ |
| Tryptophane | Vitamin $B_{12}$ |
| Tyrosine | Biotin |
| Valine | Pantothenic acid |
| Glutamic acid | Choline |
| Glycerine | Inositol |
| Isoleucine | Para-amino Benzoic acid |
| Proline | Bee Pollen |
| Phenylaline | Evening Oil of Primrose |
| Methionine | Aloe Vera |
| Histidine | Vitamin K |
| Leucine | Chromium |
| Lysine | Vitamin E |
| Cystine | Vitamin C |
| Copper | Magnesium |
| Calcium | |

Once the additional or supplemental ingredients are added to the base composition, the overall composition used in the treatment may be applied as described above, with exposure to sunlight also being most preferred during the treatment.

The following examples are given as specific illustrations of the claimed invention. It should be understood, however, that the specific details set forth in the examples are merely illustrative and in nowise limitative. All parts and percentages in the examples and the remainder of the specification are by weight unless otherwise specified.

In preparing the composition used in the following examples, various batch compositions were first prepared as follows using commercially available ingredients:

BASIC COMPOSITION

| | |
|---|---|
| Live yeast cells (saccharomyces cerevisial) | about 6 parts |
| Selenium (powdered) | about ½ part |
| Carotene (beta) | about 1 part |
| RNA | about 3 parts |
| DNA | about 2 parts |
| Water | about 3 parts |
| Albumen | about 1 part |

AMINO ACID CONTAINING COMPOSITION

| | |
|---|---|
| Alanine | 1.992 g. |
| Arginine | 1.272 g. |
| Aspartic acid | 2.802 g. |
| Serine | 1.464 g. |
| Threonine | 1.314 g. |
| Tryptophane | .378 g. |
| Tyrosine | .810 g. |
| Valine | 1.584 g. |
| Glutamic acid | 4.476 g. |
| Glycine | 1.338 g. |
| Isoleucine | 1.320 g. |
| Proline | .822 g. |
| Phenylalanine | 1.206 g. |

| -continued | |
|---|---|
| Methionine | .438 g. |
| Histidine | .672 g. |
| Leucine | 1.974 g. |
| Lysine | 2.178 g. |
| Cystine | 162 g. |

VITAMIN CONTAINING COMPOSITION

| | |
|---|---|
| Folic acid | .108 g. |
| Vitamin $B_1$ | .002 g. |
| Vitamin $B_2$ | .0025 g. |
| Niacin | .018 g. |
| Vitamin $B_6$ | .950 g. |
| Vitamin $B_{12}$ | .0003 g. |
| Biotin | .03 g. |
| Pantothenic acid | 1.2 g. |
| Choline | .230 g. |
| Inositol | .190 g. |
| Para-amino Benzoic acid | .0015 g. |

SUPPLEMENTAL COMPOSITION

| | |
|---|---|
| Bee Pollen | 420 g. |
| Evening Oil of Primrose | 210 g. |
| Aloe Vera | 75 ml. |

EXAMPLE 1

A composition was prepared using 8½ parts by weight by the basic composition, ½ part by weight of the amino acid containing compostion, ½ part by weight of the vitamin containing composition and ½ part by weight of the supplemental composition. This composition was used in a treatment of an 80 year old female Caucasian, having a fair complexion. Prior to the treatment, the woman's face exhibited extreme sagging in the skin, the eyes were very much affected due to a depletion of skin elasticity and the natural aging process and could not be completely closed except when lying down. There were heavy, deep set lines around the eyes, mouth, forehead, neck and chin. The tone of the muscles and skin was also very bad.

Five treatments were administered within a period of four days. Each treatment was as that described in Example 1. A rapid change was noticed in the skin with the treatments. The skin around the eye area was completely reversed and the gap between the lower eye socket and the mucus membrane was completely sealed together. Most of the lines disappeared, the skin become 75% firmer than before the treatment and much of the sagging was eliminated. The coloring of the skin was also much more even. Overall, the entire face took on a glow and had a much more youthful appearance.

EXAMPLE 2

A composition such as that prepared in Example 4 was applied to the skin of a 45 year old Caucasian female having a fair complexion, some freckles, and dry skin. The application of the composition was made to the face, chest, neck and breasts. Prior to the treatment, fatty pockets were evident under the eyes, deep set lines were apparent under and at the side of the eyes, the woman's coloring and texture was uneven and there was cracking of the and lower lips at the boarders of the mouth. As well, generally poor muscle and skin tone was apparent.

The woman was treated for five consecutive days, one treatment each day. Each treatment consisted of 45 minutes to one hour, with the composition then being removed. The change in the complexion and skin was quite evident. The bags under the eyes and the sagging skin was completely reversed, with the fatty pockets under the eyes being gone. The treatment to the chest, neck and upper breasts produced the same results. the lines and gaps, as well as the cracks around the mouth, were not detectable and the texture of the skin was greatly improved.

EXAMPLE 3

A formulation comprising 8½ parts by weight of the basic composition, ½ part by weight of the amino acid containing composition, ½ part by weight of the vitamin containing composition and ½ part by weight of the supplemental composition was used in the treatment of an elderly lady having extensive sagging and wrinkling around the eyes. The treatments were as disclosed in Example 1, and occurred once a day for two weeks, with the exposure being to natural sunlight for a period of time of about 40 minutes each day. After the two week treatment, the majority of wrinkles and sagging around the eyes has been reversed.

EXAMPLE 4

In this example, a middle aged male of about 46 years was treated for extensive swelling of the lower eyelids and large pockets of fat and fluid buildup underneath the eyes. The client had been on regular doses of cortisone. The formulation used comprised the basic composition ingredients, 9 parts by weight, and 1 part by weight of the supplemental composition, along with 2.1 milligrams of calcium, 60 milligrams of magnesium, 18 milligrams of niacin and 5.7 milligrams of copper. The formulation was applied once a day, with the applied formulation being exposed to natural sunlight for a period of about 25 minutes. As the treatment progressed, the extensive swelling was reduced and the large pockets of fat and fluid buildup under the eyes were also noticeably reduced.

Thus, from the foregoing, it can be seen that by using the basic composition, either alone or in combination with the various other ingredients, very beneficial cosmetic, as well as therapeutic, results can be elicited with regard to problem skin disorders. In all of the Examples, an exposure to sunlight or artificial sunlight was employed. This has been found to be most beneficial. Without the exposure, however, the benefits would as well be achieved, but not nearly as fast, as significant or as long lasting.

Although the invention has been described with preferred embodiments, it is to be understood that variations and modifications may be resorted to as will be apparent to those skilled in the art. Such variations and modifications are to be considered within the purview and the scope of the claims appended hereto.

What is claimed is:

1. A beautifying and moisturing composition for dermal application, which comprises cosmetic effective amounts of the following components in parts by weight:

| | |
|---|---|
| live yeast cells, | about 5 to about 8 parts |
| selenium, | about ¼ to about ¾ part |
| carotene, | about ¾ to about 1½ parts |

| | |
|---|---|
| RNA, | about 2 to about 4 parts |
| DNA, | about 1 to about 3 parts |
| water and | about 2 to about 6 parts |
| albumen, | about ¾ to about 2¼ parts. |

2. The composition of claim 1, wherein the live yeast cells are saccharomyces cerevisial and the selenium is of a finely powdered form.

3. The composition of claim 1, wherein the composition comprises about 6 parts live yeast cells, about ½ part selenium, about 1 part carotene, about 3 parts RNA, about 2 parts DNA, about 3 parts water and 1 part albumen.

4. The composition of claim 3, wherein the live yeast cells are saccharomyces cerevisial and the selenium is finely powdered.

5. The composition of claim 1, wherein the composition further comprises at least one of the following supplemental ingredients:

| | |
|---|---|
| Alanine | Folic acid |
| Arginine | Vitamin B$_1$ |
| Aspartic acid | Vitamin B$_2$ |
| Serine | Niacin |
| Threonine | Vitamin B$_6$ |
| Tryptophane | Vitamin B$_{12}$ |
| Tyrosine | Biotin |
| Valine | Pantothenic acid |
| Glutamic acid | Choline |
| Glycerine | Inositol |
| Isoleucine | Para-amino Benzoic acid |
| Proline | Bee Pollen |
| Phenylaline | Evening Oil of Primrose |
| Methionine | Aloe Vera |
| Histidine | Vitamin K |
| Leucine | Chromium |
| Lysine | Vitamin E |
| Cystine | Vitamin C |
| Copper | Magnesium |
| Calcium. | |

6. The composition of claim 1, wherein the supplemental ingredients comprise from 5 to about 20 percent by weight of the entire composition.

7. The composition of claim 1, wherein the composition further comprises a combination of the following supplemental ingredients in an amount of less than about 20 percent by weight of the total composition:

| | |
|---|---|
| Alanine | Glycine |
| Arginine | Isoleucine |
| Aspartic acid | Proline |
| Serine | Phenylalanine |
| Threonine | Methionine |
| Tryptophane | Histidine |
| Tyrosine | Leucine |
| Valine | Lysine |
| Glutamic acid | Cystine. |

8. The composition of claim 1, wherein the composition further comprises a combination of the following supplemental ingredients in an amount of less than about 20 percent by weight of the total composition:
Folic acid
Vitamin B$_1$
Vitamin B$_2$
Niacin
Vitamin B$_6$
Vitamin B$_{12}$
Biotin
Pantothenic Acid
Choline
Inositol
Para-amino Benzoic acid.

9. The composition of claim 1, wherein the composition further comprises a combination of the following supplemental ingredients in an amount of less than about 20 percent by weight of the total composition:
Bee Pollen
Evening Oil of Primrose
Aloe Vera.

10. The composition of claim 1, wherein the composition comprises 8½ parts by weight of a combination of the following components
live yeast cells,
selenium,
carotene,
RNA,
DNA,
water and
albumen;
and further comprises ½ part by weight of a combination of the following components:

| | |
|---|---|
| Alanine | Glycine |
| Arginine | Isoleucine |
| Aspartic acid | Proline |
| Serine | Phenylalanine |
| Threonine | Methionine |
| Tryptophane | Histidine |
| Tyrosine | Leucine |
| Valine | Lysine |
| Glutamic acid | Cystine |

½ part by weight of a combination of the following components:
Folic acid
Vitamin B$_1$
Vitamin B$_2$
Niacin
Vitamin B$_6$
Vitamin B$_{12}$
Biotin
Pantothenic acid
Choline
Inositol
Para-amino Benzoic acid
and ½ part by weight of a combination of the following components:
Bee Pollen
Evening Oil of Primrose
Aloe Vera.

11. A method for cosmetically treating the skin to thereby moisturize and beautify the skin which comprises applying the composition of claim 1 to the area of skin to be treated for a sufficient length of time to elicit its cosmetic beneficial results, removing the composition, and then repeating the application periodically.

12. The method of claim 11, wherein the composition is exposed to natural or artificial sunlight subsequent to the application of the composition to the area of skin to be treated.

13. The method of claim 12, wherein the duration of the exposure is in the range of from about 15 minutes to about 60 minutes.

14. The method of claim 12, wherein the duration of the exposure is in the range of from about 20 to 25 minutes.

15. The method of claim 12, wherein the composition is applied in several layers.

16. The method of claim 15, wherein the composition was applied in three layers, the first layer being applied as a thin layer which is massaged into the area of the skin to be treated;

the second layer being applied so that the composition thinly covers the skin area to be treated, and the third layer being applied so that the composition provides a thick cover over the area of the skin to be treated.

* * * * *